United States Patent
Heyne et al.

(10) Patent No.: US 9,541,497 B2
(45) Date of Patent: Jan. 10, 2017

(54) MEASUREMENT DEVICE AND METHOD FOR ANALYZING A SAMPLE GAS BY INFRARED ABSORPTION SPECTROSCOPY

(75) Inventors: Karsten Heyne, Grossbeeren (DE); Tom Rubin, Berlin (DE)

(73) Assignee: HUMEDICS GMBH, Grossbeeren (DE)

( * ) Notice: Subject to any disclaimer, the term of this patent is extended or adjusted under 35 U.S.C. 154(b) by 102 days.

(21) Appl. No.: 13/143,074

(22) PCT Filed: Dec. 21, 2010

(86) PCT No.: PCT/EP2010/070407
§ 371 (c)(1),
(2), (4) Date: Jun. 30, 2011

(87) PCT Pub. No.: WO2011/076803
PCT Pub. Date: Jun. 30, 2011

(65) Prior Publication Data
US 2011/0270113 A1 Nov. 3, 2011

(30) Foreign Application Priority Data

Dec. 24, 2009 (DE) .................. 10 2009 055 320

(51) Int. Cl.
*A61B 5/08* (2006.01)
*G01N 21/3504* (2014.01)
(Continued)

(52) U.S. Cl.
CPC .......... *G01N 21/3504* (2013.01); *A61B 5/082* (2013.01); *A61B 5/0836* (2013.01); *G01N 21/39* (2013.01);
(Continued)

(58) Field of Classification Search
CPC ....... A61B 5/082; A61B 5/087; A61B 5/0836; A61M 2230/432; A61M 16/12
(Continued)

(56) References Cited

U.S. PATENT DOCUMENTS 3,649,199 A 3/1972 Littlejohn
4,522,204 A 6/1985 Kurahashi et al.
(Continued)

FOREIGN PATENT DOCUMENTS

DE 199 40 280 C2 3/2001
EP 2 311 552 A1 4/2011
(Continued)

OTHER PUBLICATIONS

Neuhaus ("Diode Laser Locking and Linewidth Narrowing". TOPTICA Photonics AG; Sep. 2009).*
(Continued)

*Primary Examiner* — Jacqueline Cheng
*Assistant Examiner* — Puya Agahi
(74) *Attorney, Agent, or Firm* — Maschoff Brennan

(57) ABSTRACT

A measurement device and a method for analyzing a sample gas by infrared absorption spectroscopy are described. The measurement device comprises a narrowband laser having a line width of less than 0.2 cm$^{-1}$ and being smaller than a width of an infrared absorption line to be measured of a sample gas. The measurement device is suited and can be arranged to measure the respiratory gas of a human or animal as sample gas, wherein the respiratory gas exchanges in the measurement chamber only by the respiration of the human or animal, and the respiratory resistance of the measurement device is less than 60 mbar.

16 Claims, 7 Drawing Sheets

(51) Int. Cl.
    *A61B 5/083*     (2006.01)
    *G01N 21/39*     (2006.01)
    *A61B 5/087*     (2006.01)
    *A61M 16/12*     (2006.01)

(52) U.S. Cl.
    CPC ............... *A61B 5/087* (2013.01); *A61M 16/12* (2013.01); *A61M 2230/432* (2013.01); *G01N 2800/085* (2013.01)

(58) Field of Classification Search
    USPC ........ 600/529, 531, 532, 538, 539, 540, 543
    See application file for complete search history.

(56) References Cited

U.S. PATENT DOCUMENTS

| | | | |
|---|---|---|---|
| 4,572,208 | A * | 2/1986 | Cutler et al. ................. 600/531 |
| 5,042,501 | A | 8/1991 | Kenny et al. |
| 5,317,156 | A | 5/1994 | Cooper et al. |
| 5,331,409 | A | 7/1994 | Thurtell et al. |
| 5,645,071 | A | 7/1997 | Harnoncourt et al. |
| 6,216,692 | B1 * | 4/2001 | Todokoro et al. ....... 128/205.23 |
| 6,512,581 | B1 | 1/2003 | Yamamori et al. |
| 6,538,728 | B1 | 3/2003 | Stolle |
| 6,581,595 | B1 * | 6/2003 | Murdock et al. ........ 128/204.18 |
| 6,656,127 | B1 | 12/2003 | Ben-Oren et al. |
| 2004/0211905 | A1 | 10/2004 | Hancock et al. |
| 2005/0008542 | A1 | 1/2005 | Yeh |
| 2005/0288602 | A1 * | 12/2005 | Hoppe et al. ................ 600/532 |
| 2007/0081162 | A1 | 4/2007 | Roller et al. |
| 2008/0061238 | A1 | 3/2008 | Hok et al. |
| 2008/0289628 | A1 * | 11/2008 | Hallback et al. ........ 128/203.12 |
| 2008/0315102 | A1 * | 12/2008 | Weidmann ............... 250/339.01 |
| 2009/0124918 | A1 * | 5/2009 | Stockmann et al. .......... 600/532 |
| 2009/0131810 | A1 | 5/2009 | Oren et al. |
| 2009/0173350 | A1 * | 7/2009 | Swanson .................. 128/207.18 |
| 2009/0303486 | A1 | 12/2009 | Magari et al. |
| 2010/0143880 | A1 | 6/2010 | Stockmann |

FOREIGN PATENT DOCUMENTS

| | | |
|---|---|---|
| EP | 2 347 818 A1 | 7/2011 |
| GB | 2312743 A | 11/1997 |
| JP | 54-128863 A | 10/1979 |
| JP | S58-223040 A | 12/1983 |
| JP | 02-307518 A | 12/1990 |
| JP | 05-340872 A | 12/1993 |
| JP | H07-503319 A | 4/1995 |
| JP | H08-500043 A | 1/1996 |
| JP | H10-248826 A | 9/1998 |
| JP | 2000-074822 A | 3/2000 |
| JP | 2007-090262 A | 4/2007 |
| JP | 2008-026397 A | 2/2008 |
| JP | 2008-070369 A | 3/2008 |
| WO | WO 99/61895 A1 | 12/1999 |
| WO | 2007/000145 A2 | 1/2007 |
| WO | 2007/054940 A2 | 5/2007 |
| WO | 2007/107366 A1 | 9/2007 |
| WO | 2008/057662 A2 | 5/2008 |
| WO | 2009/101374 A1 | 8/2009 |

OTHER PUBLICATIONS

Bowling et al. ("Tunable diode laser absorption spectroscopy for stable isotope studies of ecosystem-atmosphere CO2 exchange". Agricultural and Forest Meteorology 118 (2003) pp. 1-19).*

Weidmann et al.: "Development of a compact quantum cascade laser spectrometer for field measurements of CO2 isotopes", Applied Physics B, Laser and Optics, Springer Berlin, vol. 80, No. 2, Feb. 2005, p. 255-260.

XP007918339: Anonymous, "Atmung" Apr. 18, 2011, p. 1-9.

JP Office Action dated Apr. 22, 2014 as received in Application No. 2012-545298 (English Translation).

\* cited by examiner

MEASUREMENT DEVICE AND METHOD FOR ANALYZING A SAMPLE GAS BY INFRARED ABSORPTION SPECTROSCOPY

CROSS-REFERENCE TO A RELATED APPLICATION

This application is a National Phase Patent Application of International Patent Application Number PCT/EP 2010/070407, filed on Dec. 21, 2010, which claims priority of German Patent Application Number 10 2009 055 320.7, filed on Dec. 24, 2009.

BACKGROUND

The invention relates to a measurement device for analyzing a sample gas by infrared absorption spectroscopy as well as an according method.

Since centuries it is known that the respiratory odor is an indicator for a possible disease—the most prominent example is the sweetish-fruity odor caused by acetone in diabetes mellitus type I. Even the odor of healthy humans contains several hundred volatile chemical compounds, so-called volatile organic compounds (VOCs) in low concentration (ppm to ppt range). Some of these play an important role in physiological or patho-physiological processes. If a disease is present, the concentration of certain trace gases increases in the breath. In some diseases, also gases can be detected which do not occur in the healthy organism. Thus, the respiratory gas analysis has a big potential for the clinical diagnostics and therapy monitoring. However, the trace gas concentration is often so low that it cannot be measured sufficiently exact with the available gas-analytical methods.

There exist highly sensitive detection methods like e.g. the mass spectroscopy or the FTIR-spectroscopy in multi-pass sample cells. However, such detection devices cannot be applied directly to a patient and are, consequently, of no relevance for the clinical daily routine. This is also due to the fact that the evaluation needs several days and that non-calculable sources of error occur due to the transport of the samples. Mobile constructions in the area of the infrared absorption spectroscopy having diode lasers (e.g. lead salt lasers) as light sources are also in use since several decades, they could, however, until now not achieve the necessary stability over a longer time period for the sensitive detection of gases so that also in this case the use remained restricted to the medical basic research.

An alternative method is the so-called NDIRS-method (NDIRS-non-dispersive IR spectroscopy). It detects density fluctuations in the sample gas which are triggered by absorption of infrared light. This detection method is sensitive and can perform a measurement every two and a half minutes. However, the measurement results are biassed by other gases like e.g. oxygen so that this method can only be restrictively used in the clinical daily routine.

Another method is used by the company Oridion Systems Ltd. under the denomination BreathID®. Here, a $CO_2$ pressure lamp is used as light source. However, this method is strongly restricted in its sensitivity and speediness by occurring line width fluctuations (in the lamp and in the sample gas), low light intensities and spectral fluctuations and, thereby, does not provide 15 highly sensitive measurement results in short time. The NDIRS method and the method of Oridion Systems Ltd. are well suited for e.g. the detection of the bacterium *Helicobacter pylori* in the stomach of a patient. The presence of the bacterium is detected in a qualitative manner by an increased $^{13}CO_2$ content in the exhalation air after application of a $^{13}C$-labelled diagnostic.

Qualitative test methods become of no importance if the test lies within the same price segment like the treatment. A further strategy to guarantee the simple and fast detection of volatile chemical compounds is the use of surface-sensitive microchips which select and bind special trace gases from the respiratory air. Thereby, a sensitive detection of these volatile chemical compounds is possible and the qualitative decision whether or not the patient is ill can be made.

The mere detection of a disease is Instructive; however, it does not provide any information on a suited therapy. Thus, the future of respiratory gas analysis lies in the quantitative determination of the degree of disease which offers the physician a direct determination aid for the therapy. If such tests can be carried out simply and quick and the results are immediately present in a comprehensible form for the physician, the test can become accepted in the clinical daily routine.

The requirements for quantitative respiratory gas tests are high: For unambiguously identifying the trace gases, a high selectivity and detection sensitivity is necessary since the concentration lies often in the ppm to ppb range. The exact quantitative determination of the trace gas amount has to be guaranteed. Additionally, the measurements should occur online and in real-time to avoid a laborious and error-prone sample collection (e. g. in bags or in side stream). For a feasible and economic use, simple operation, compactness, robustness, low maintenance effort and/or a favorable cost-benefit ratio are to be required. These high and manifold requirements can currently not be completely met by any gas analytic method.

The exhaled air of humans has a carbon dioxide volume fraction of 2% to 4% and is exhaled in 10 to 20 breaths per minute, by infants and newborns even in 25 to 50 breaths per minute. The respiratory pressure of humans is approximately 50 mbar to maximal 160 mbar, at a volume of approximately 0.5 l. Only approximately 70% of the respiratory air reach the lung so that also in only approximately 70% of the gas volume a significantly increased carbon dioxide fraction is present. In the remaining gas volume—the dead space volume—the carbon dioxide concentration can decrease just onto the concentration of the ambient air of approximately 0.04%. This results in that the carbon dioxide concentration in the respiratory air can fluctuate by 2 orders of magnitude from 0.04% to 4%. Carbon dioxide concentrations of over 5% are toxic and can e.g. lead to headaches and cramps.

The produced carbon dioxide amount depends on the individual metabolism of each single human. Different approximation methods are used to estimate the carbon dioxide production of a human. The influencing parameters are e.g. body weight and body surface. The body surface is in turn often estimated by the body size and the body height so that it is often calculated with only moderately exact parameters in the medical science, strongly restricting a quantitative result evaluation or making it even impossible.

For a direct quantitative determination of metabolism processes or metabolisms it is necessary to track the dynamics of the process in a time-resolved manner, at the best in real time. If the metabolism dynamics exhibits a kinetics which can be modelled by a first order differential equation (first order dynamics), the maximum of the kinetics A and the time constant tau can be determined by solving the differential equation or by fitting an exponential function $y(t)=A*\exp(-t/\text{tau})$. Quantitative metabolic parameters can then be determined from the parameters A and tau. Triggering of the metabolism dynamics is at the best achieved by the short-term initiation, e.g. by an i.v. application of a diagnostics or by releasing a diagnostic by a light exposure/irradiation.

If the release or the start of the dynamics takes longer than the slope tau or than a breath, the dynamics of the release has to be separately determined and to be deconvoluted from the metabolism dynamics. An example of a fast metabolism start is the i.v. application of the diagnostic $^{13}C$ methacetin in bolus. It is distributed with the blood (approximately 60 heart beats per minute) in the body and reaches in approximately I second the liver where it is metabolized to paracetamol and $^{13}CO_2$. The start of the dynamics is much faster than the respiratory rhythm and thus leads to a first order dynamics which can be directly evaluated. If the SC-methacetin is, however, orally applied, the adsorption in the stomach leads to a convolution of the dynamics with the stomach adsorption dynamics which significantly biases the dynamics.

To monitor the metabolism dynamics in real time, each breath should be measured with a very high sensitivity. This means that the respiratory air in the measurement chamber has to be rapidly exchanged and that a complete evaluation of the breath must have been occurred in less than two seconds.

An analysis method enabling a quantitative determination of the liver function is disclosed in WO 2007/000145 A2. This method is based on a substrate accumulation of the substrate to be metabolized in the liver and the determination of the maximal reaction rate of the substrate, enabling conclusions on the liver function capacity of a patient.

From WO 2007/107366 A1, a generic device for the spectroscopic analysis of a gas is known in which a sample gas continuously flows through a measurement chamber.

SUMMARY

It is an object of the present invention to ameliorate the measurement device known from WO 2007/107366 A1 and the measurement method used there with the aim to carry out measurements in real time.

According to an aspect of the invention, this object is achieved by a measurement device having the features as set forth below and a method having the features as set also forth below. Embodiments of the invention are also specified.

According to this, the solution according to an aspect of the invention makes provision of the use of a narrow band emitting laser. As narrow band emitting laser a laser is considered, the line width of which is chosen such that it is smaller or equal to the width of the absorption line to be measured of the sample gas. Furthermore, provision is made that the laser frequency varies periodically within a defined spectral range, wherein the laser frequency and its variation are chosen such that at least one absorption line to be measured of the sample gas lies within the defined spectral range. The periodic variation of the laser frequency (also referred to as tunability) is thereby attended by a defined spectral range which is measured during each period of this frequency variation. At least one absorption line to be measured lies within this spectral range.

According to an aspect of the invention, provision is furthermore made that the detection device is designed and arranged to detect the light being emitted from the laser and radiated through the measurement chamber in such a time-resolved manner that the light absorption can be detected frequency-resolved within the defined spectral range.

Thereby, the detection device carries out a single absorption measurement within $10^{-5}$ seconds or faster, in particular within $10^{-6}$ seconds or faster. By this fast measurement, a spectral range, which is measured by the variation of the laser frequency, can be detected frequency-resolved. The measured spectral range is thereby measured with a plurality of measuring points, e.g. with 20, 100, 500 or 1000 measurements points, which correspond in each case to an absorption measurement.

The high time resolution of the absorption measurements makes it possible to detect a spectral range, which is defined by a variation of the laser frequency and in which at least one absorption line to be measured lies, in a frequency-resolved manner with a high point density of single measurements within the spectral range. This is connected to several properties.

Thus, the high time resolution and the thereby achievable high point density of measuring values of a spectral range measured during a frequency variation is attended by a high measurement accuracy. This is further increased if an averaging over several spectra detected one after each other is effected, as provision is made for in an implementation variant.

The high time resolution, the high spectral resolution (achieved by a high point density of the single measurements) and a high sensitivity make it possible to measure absorption lines with the sensitivity in the ppb range. Such sensitivity is essentially necessary to guarantee e.g. the use of the measurement device for the quantitative detection of metabolized substrates.

Furthermore, the measurement device is in particular suited and can be arranged to measure the respiratory gas of a human or animal as sample gas, wherein the respiratory gas exchanges in the measurement chamber only by the respiration of the human or the animal, and the respiratory resistance of the measurement device is less than 60 mbar, in particular less than 50 mbar and very particular less than 40 mbar. This means, no pumps or other devices are necessary to transport the sample gas through the measurement device. In other words, the counter pressure established by the measurement device is less than 60 mbar in particular less than 50 mbar and very particular less than 40 mbar. Such a low counter pressure can be overcome without technical utilities by an accordingly high pressure (which is e.g. generated by the respiration of a human or animal).

If measurements are carried out in flow-through of the sample gas through the measurement chamber, furthermore temporal variations of the composition of the sample gas can be detected in real time with a high resolution. It is e.g. possible to determine changes of isotopic ratios in the respiratory gas in real time, and this at carbon dioxide concentrations of the respiratory gas in the range between 0.08% and 8%.

In an embodiment of the invention, provision is made that the laser frequency and its variation are chosen such that at least two absorption lines of the sample gas lie within the defined spectral range. This makes it e.g. possible to determine the ratio of two isotopes of the sample gas on the basis of the light absorption occurring at two absorption lines. The isotopes are e.g. $^{13}CO_2$ and $^{12}CO_2$. Not only atoms having the same proton number but a different mass number are in this context referred to as isotopes, but also molecules containing such different atoms. Instead of the ratio of two isotopes, also the ratio of two elements (having different proton numbers) or two molecules can be determined on the basis of two or more absorption lines.

The determination of the ratio of two isotopes, elements or molecules furthermore enables the determination of absolute values of the respective isotopes, elements and molecules also at fluctuating concentration. E.g., by the determination of the $CO_2$ content in the respiratory air, fluctuations of the concentration of the $CO_2$ of 0.04% to 4% occur during breathing. The extent of fluctuation can be detected by determining the absolute content of $^{12}CO_2$ (e.g. per breath). Thereby, the absolute content of the isotope $^{13}CO_2$ can be determined which is in a fixed natural ratio to $^{12}CO_2$. Additionally, changes due to an additional metabolism of $^{13}CO_2$ can be detected by an evaluation of the variation of the ratio of both isotopes.

The high resolution and point density of the measurement device according to an aspect of the invention make it possible to determine the ratio of two isotopes, elements and molecules in real time. This is particularly interesting if the ratio changes over time. In an embodiment, a display is assigned to the evaluation unit for this case, displaying the variation of the ratio over time.

The measurement device according to an aspect of the invention can be designed mirror-less, wherein the light being emitted from the laser passes through the measurement chamber exactly once. Thereby, a simple optical construction with the low rate of failures is provided. In contrast to the measurement chamber of WO 2007/107366 A1 no mirrors are thus present in the measurement chamber, on which mirrors the laser light would be reflected several times. The measurement chamber comprises only an inlet window through which laser light enters the measurement chamber and an outlet window through which the transmitted light exits the measurement chamber.

In a further embodiment, the measurement device comprises tempering means (in particular heating means) which temper, in particular heat, the measurement chamber and existing windows onto a constant temperature, which is e.g. at more than 35° C. Thereby, it is prevented that water vapor being eventually present in the sample gas gets steamed up on the measurement chamber. Cooling the measurement chamber is also thinkable.

In a further embodiment of the invention, provision is made that a sample gas flows through the measurement chamber continuously or intermittently. For this purpose, the measurement chamber has, in an embodiment, an open construction without valves or air flaps which could hinder the flow of sample gas into and out of the measurement chamber. In an embodiment, provision is furthermore made that the measurement device has an essentially constant cross section for the gas flowing through between the gas inlet into the measurement device and gas outlet out of the measurement device. Thereby, a laminar flow is provided at all locations of the measurement device and it is prevented that gas accumulates at certain locations and is not replaced by new sample gas.

In a variant, the measurement device comprises at least section-wise, in particular within the whole measurement chamber, a constant cross section so that at least section-wise a laminar flow is established in the measurement device. If, e.g., the whole measurement chamber has a constant cross section, an essentially laminar flow of the sample gas is guaranteed in operation within the whole measurement chamber. Thereby, very precise measurements are made possible in a particular suited manner.

In a further embodiment, a supply of sample gas into the measurement chamber and the drain of sample gas from the measurement chamber are effected in a direction which is perpendicular to the direction in which the light passes through the measurement chamber. This assures that the gas supply and gas drain as well as according adapters do not interfere the laser light. In an embodiment, Gas supply and gas drain are thereby arranged offset so that the sample gas flows to some extent in the direction of the laser beam through the measurement chamber.

In an embodiment, the measurement device is designed such that a time-resolved light detection by the detection device is effected during flowing-through of the sample gas through the measurement chamber. Infrared absorption measurements are thus carried out in each phase of the gas flow, in particular also when the sample gas flows through the measurement chamber. The absorption measurements take place in real flow-through (i.e. in flow-through measuring technique).

In a further embodiment, the measurement device comprises a spirometer which detects the volumetric flow of the sample gas flowing through the measurement chamber. Thereby, provision can be made that the sample gas flows through the spirometer after flowing through the measurement chamber, for which case it then exits the measurement device through the spirometer. Generally, the spirometer can be arranged at any location between gas inlet into the measurement device and gas outlet out of the measurement device within the measurement device.

The measurement of the volumetric flow makes it possible to determine absolute total amounts of certain molecules of a defined gas amount corresponding e.g. to the gas amount of a breath of a human or animal. In particular, the concentration can be determined directly from the absorption since the extinction coefficient of each absorption line is known and the length of the measurement chamber also. Since the absorption and—by the spirometer—the volumetric flow rate can be monitored time-resolved in real time, the total amount can be determined by an integration of the product of volume and concentration over time in real time.

In an embodiment, provision is furthermore made for an ante-chamber through which the sample gas flows into the measurement chamber. In an embodiment, the ante-chamber is thereby designed to heat or cool the sample gas onto a defined temperature and to thereby reduce the water vapor content of the sample gas.

In a further embodiment, the ante-chamber is alternatively or additionally designed to reduce the water vapor content of the sample gas onto at least 60% relative humidity. In an embodiment, the reduction of the water vapor content is effected by semi-permeable membranes which exclusively allow an exchange of water vapor (but not of other substances). The air outside the membrane must have a relative humidity of less than 50% relative humidity. If the water vapor content outside the ante-chamber is lower than inside, then the water vapor content of the sample gas flowing through the ante-chamber is reduced. The total area of the membrane determines how much gas exchange can take place.

As example, the application of the measurement device for the breath analysis may be mentioned in which a single breath (in particular a complete breath) is analyzed. The humidity in a breath is often more than 90% relative humidity which is reduced by the semi-permeable membrane in the ante-chamber to less than 50% relative humidity. The active area of the semi-permeable membrane can thereby, e.g., be more than 150 $cm^2$, in particular more than 200 $cm^2$ and very particular more than 250 $cm^2$.

In a further embodiment, the ante-chamber is alternatively or additionally designed to homogenize the sample gas. The homogenization of the single sample gas is effected by different (at least two) branchings of different length and diameter through which parts of the sample gas pass through. After the area of the branchings, the parts of the sample gas are brought together again. Thereby, it is important that the total cross section of all branchings (i.e. the sum of the cross sections of the single branchings) has a bigger or an equally big flow cross-section than the rest of the measurement device so that no increased or only a slightly increased pressure resistance for the flow of the sample gas in the measurement device is generated by the branchings. The lengths of the different branchings through which the sample gas flows are chosen such that sample gas volumes of a certain volume size are optimally mixed. The mixing takes place exclusively passive and uses only the pressure difference to the outlet of the measurement device which induces the sample gas to flow.

As an example, the application of the measurement device for the breath analysis may be mentioned in which a single (in particular total) breath is homogenized. The exhalation generates the pressure difference which induces the sample gas to flow. The average volume of a breath is approximately 500 ml. Already at branchings having three different diameter sizes with ratios 3:d2:d1=3:2:1 the laminar volume flow shows different velocities v3<v2<v1. If the total average of the single diameter sizes d1, d2 and d3 is held constant by choosing several branchings having a diameter size d1 and 2, then approximately the same volume flows through all branchings having the same diameter (disregarding friction). By means of the different flow velocities of the sample gas, the desired volume amount (e.g. 500 ml) can now be well mixed by choosing the branching length. The number of branchings is at least 2. The more branchings are used, the more homogeneous the sample gas can be mixed. A good mixing makes possible a more precise and faster measurement of gas components in the sample gas. It is important for e.g. highly precise measurements in flow-through measurement technique.

In an embodiment, the diameters of the single branchings are chosen such that a second branching has an at least 50%, in particular at least 60%, in particular at least 70%, in particular at least 80%, in particular at least 90% and very particular at least 100% bigger diameter than a first branching.

The narrow band emitting laser has in an embodiment of the invention a line width of less than 0.2 $cm^{-1}$, in particular of less than 0.05 $cm^{-1}$. The smaller the line width, the more precise a certain spectral range can be measured. In an embodiment, the laser is an infrared quantum cascade laser which e.g. emits light in the frequency range between 2200 $cm^{-1}$ and 2400 $cm^{-1}$, in particular in the range between 2295 $cm^{-1}$ and 2305 $cm^{-1}$.

For the variation of the frequency of the laser, means for tuning the laser are provided in an implementation variant which means apply a periodically modulated voltage to the laser head of the laser, wherein the applied voltage is attended by a short-term temperature increase and therewith by a frequency shift. Thus, by an according voltage modulation, a repeated temperature increase and temperature decrease of the laser can be achieved. In an embodiment, the tunability of the laser thereby lies between 0.5 $cm^{-1}$ and 60 $cm^{-1}$, in particular at 1 $cm^{-1}$, 2 $cm^{-1}$, 6 $cm^{-1}$ or 20 $cm^{-1}$. The frequency variation determines the spectral range which is measured. The modulation frequency determines by which frequency a certain spectral range is measured. The modulation frequency is in an embodiment between 1 and 500 Hz, in particular between 100 and 500 Hz, in particular between 10 and 100 Hz, in particular at approximately 50 Hz. In an embodiment, the voltage applied to the laser head is a triangle voltage so that a defined frequency spectrum is passed through first upwards and then again downwards. Alternatively, e.g. a saw tooth voltage can be used.

As already explained, the measurement device according to an aspect of the invention exhibits a high time resolution of the single measurements which correlates with a high point density of the measured spectrum. Thereby, the detection device is designed and arranged to measure per spectral range, in which the laser frequency varies, i.e. during a period of the modulation frequency more than 20 measuring points, in particular more than 100 measuring points, particularly more than 500 measuring points.

In an embodiment, the laser signal being emitted from the laser is pulsed and has in an embodiment a pulse duration of less than 200 ns, in particular of less than 100 ns. In an embodiment, the detection device is thereby designed and arranged to carry out an absorption measurement for each emitted light pulse of the laser. Thus, each laser pulse leads to an absorption measuring value.

Further, provision can be made that the detection device is read out with a frequency being twice as big as the frequency by which the laser emits light pulses. Thus, reading out is effected with double laser repetition rate. This means that only each second read out process relates to a measured light pulse. The read out processes lying in-between correlate with no measured signal and represent only the background signal. In an embodiment, the background signal is directly subtracted. This permits a further increase of the measurement accuracy.

To increase the measuring accuracy, provision is further made in an implementation variant that the light emitted from the laser is divided into two partial beams, wherein the one partial beam passes through the measurement chamber and the other partial beam is detected by a reference detection device. The evaluation unit evaluates the signals of the reference detection device for standardizing the signal strength of the laser. Thereby, intensity fluctuations of the laser can be computationally eliminated, increasing the accuracy of the measurement carried out further on.

The measurement device according to an aspect of the invention is in an embodiment arranged to analyze the respiratory gas of a human or an animal as sample gas. Particularly, the measurement device is suited to determine the ratio of the $^{13}CO_2/^{12}CO_2$ isotopic concentration in the respiratory gas of the human or animal in a time-resolved manner. Furthermore, a quantitative measurement of a metabolic parameter in the respirator gas can be carried out in real time. E.g. the measurement device is adapted to determine the total amount of $^{13}CO_2$ per breath. In case of a measurement of several consecutive breaths, this can be done with an accuracy of approximately 10 µg. Furthermore, the measurement device is adapted to determine the carbon dioxide concentration in the respiratory gas in the range between 0.08% and 8% in flow-through in real time.

A further application permits the determination of the line width of an absorption line of the sample gas in dependence on the gas concentration by the measurement device according to an aspect of the invention. Thus, due to the high time resolution, the high spectral resolution and the high sensitivity of the absorption measurements carried out, the line width of a considered absorption line can be determined in dependence on the gas concentration. In doing so, the line widths are measured at defined pre-adjusted gas concentrations.

Furthermore, the invention relates in an aspect to a method for analyzing a sample gas by infrared absorption spectroscopy. The method comprises the following steps:

radiating a measurement chamber with light being emitted from a narrow band laser, the line width of which is smaller or equal to the width of an infrared absorption line to be measured of a sample gas being present in the measurement chamber, wherein the laser frequency is periodically varied within a defined spectral range, and the laser frequency and its variation are chosen such that at least one infrared absorption line to measured of the sample gas lies within the defined spectral range, time-resolved detection of the light emitted by the laser and radiated through the measurement chamber, wherein a single absorption measurement is carried out within $10^{-5}$ s or faster, and evaluating the detected signals regarding a light absorption occurred in the measurement chamber, wherein the light absorption is determined frequency-resolved within the defined spectral range.

BRIEF DESCRIPTION OF THE DRAWINGS

Subsequently, aspects of the invention are explained in more detail with the aid of several exemplary embodiments referring to the Figures of the drawings.

DETAILED DESCRIPTION

Figure 1:
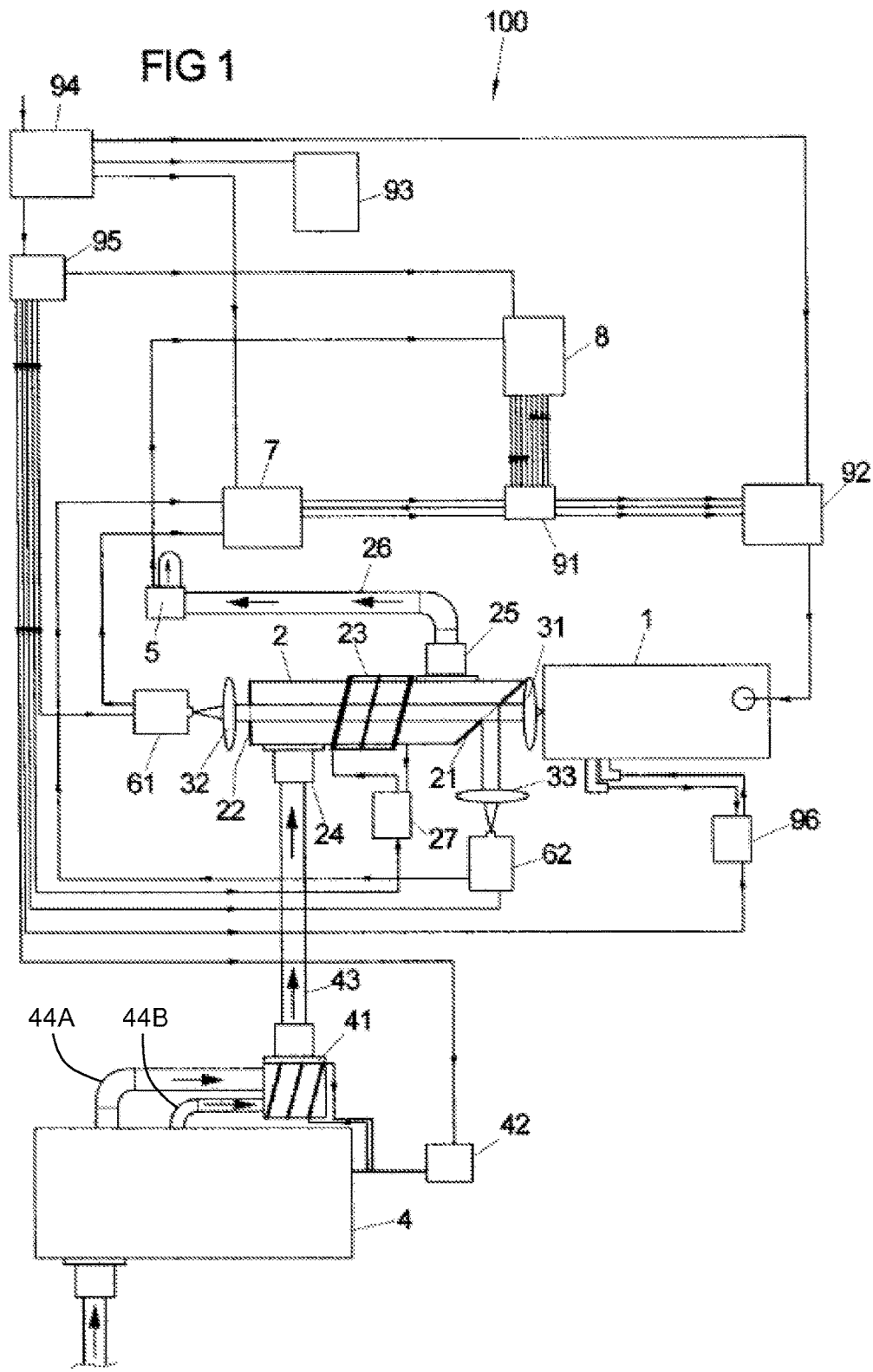
FIG. 1 shows an exemplary embodiment of a measurement device for analyzing a sample gas by infrared absorption spectroscopy.

FIG. 1 shows a measurement device 100 for analyzing a sample gas by infrared absorption spectroscopy. The device 100 comprises a laser 1, a measurement chamber 2, two detectors 61, 62, an ante-chamber 4, a spirometer 5, a charge amplifier 7 and an evaluation unit 8.

The laser 1 is an infrared quantum cascade laser (QCL), having a line width below 0.2 $cm^{-1}$, in particular a line width of 0.05 $cm^{-1}$. The basic frequency of the quantum cascade laser is adjusted by its temperature. The latter is controlled on a time scale of approximately 0.05 to 0.5 s by a laser control unit 92. The laser frequency can additionally be periodically varied within a defined spectral range. In doing so, a voltage, being referred to in the following also as "sweep voltage", is additionally applied on the quantum cascade laser 1 by the laser control unit 92. The sweep voltage and a sweep current corresponding thereto attend to a short-time temperature increase during the additional current flow in the laser and thus shift the frequency. In an embodiment, the parameters of the laser are adjusted such that once again the basic frequency is emitted directly after terminating the current flow.

The sweep voltage is continuously increased and then again decreased, e.g. by a triangular voltage or salt tooth voltage, resulting in a continuous frequency variation. Superimposing to the basic frequency, the frequency of the laser 1 is thus periodically varied. The frequency variation correlates a tunability of the laser which lies at at least 0.5 $cm^{-1}$. Examples for the width of the tunability are 1, 2, 6, 20 or 60 $cm^{-1}$. Thereby, the tunability indicates a spectral range, within which the laser frequency is varied. The modulation frequency by which the laser frequency is periodically varied, is in the range between 1 and 500 Hz. It defines how often the observed spectral range is measured. In the following, a modulation frequency of 50 Hz is assumed as an example.

The laser 1 is a pulse laser which emits light signals having a pulse duration of less than 200 ns, in particular of 100 ns or even shorter. Thereby, the maximum time resolution of a measurement is limited to 200 ns or 100 ns, respectively. Using relatively short pulse durations arranges in as much for spectrally narrow line widths, since at long lasting pulses a line broadening occurs due to a temperature increase which line broadening is connected to a comparatively long emission of laser light.

The laser rate, i.e. the number of pulses which are emitted per second, is e.g. between 10 and 100 kHz. In the following, a laser rate of 50 kHz is assumed as an example.

The laser 1 is arranged in a closed housing which prevents a contact with surrounding air. For this purpose, it is e.g. arranged in a TO3 housing. A water cooling 96 arranges for cooling the laser 1.

Furthermore, the trigger signal for the quantum cascade laser 1 is applied by a laser control unit 92.

The measurement chamber 2 has a sloped inlet window 21 through which the laser light enters the measurement chamber 2 and an outlet window 22 which is arranged perpendicularly to the optical path. The laser light emitted from laser 1 is directed to the sloped entry window 21 over an anti-reflection coated lens 31. The light is divided into two partial beams at the entry window 21. The transmitting beam crosses the measurement chamber 2, exits the measurement chamber 2 through the outlet window 22 and falls after focusing through a further anti-reflection coated lens 32 onto a first detector 61. The reflected beam falls over a further anti-reflection coated lens 33 onto a second detector 61. The anti-reflection coated lenses 31, 32, 33, which e.g. consist of ZnSe, sapphire, $CaF_2$ or $BaF_2$, are directly connected to the laser 1 or the respective detectors 61, 62 so that the measurement construction consists of only four components, namely the laser, the two detectors and the measurement chamber. This leads to a simple, robust construction.

The laser light traverses the measurement chamber 1, which is designed mirror-less, only once. This further increases the simplicity and therewith the failure immunity of the measurement construction.

The measurement chamber 2 comprises a tempering device 23 which is in particular designed as heating device and which is controlled by a temperature controller 27.

The tempering device 23 arranges for a constant temperature within the measurement chamber which lies at e.g. 35° C. or more. This prevents that water vapor eventually being present in the sample gas flowing through the measurement chamber 2 steams up the measurement chamber 2. The constant temperature can also lie beneath the ambient temperature.

The measurement chamber 2 has a first connection 24 for supplying a sample gas into the measurement chamber 2. The connection 24 is arranged at the housing of the measurement chamber consisting e.g. of aluminum. The sample gas is supplied to the measurement chamber 2 from an ante-chamber 4 via a tube 43 or the like via the connection 24. Also a heating device 41 is assigned to the ante-chamber 4 which heating device 41 conducts, via a temperature control 42, a control of the temperature of the sample gas supplied to the measurement chamber 2. Thereby, the sample gas is already heated in the ante-chamber 4 and is reduced in its water vapor content. Instead of the heating device 41, also a tempering device 41 could be used which could also cool the sample gas in the ante-chamber 4 if required.

In a further embodiment, the ante-chamber 4 is alternatively or additionally designed to homogenize the sample gas. The homogenization of the single sample gas is effected by different (at least two) branchings 44A, 44B (collectively "branchings 44") of different length and diameter through which parts of the sample gas pass through. After the area of the branchings 44, the parts of the sample gas are brought together again. Thereby, it is important that the total cross section of all branchings 44 (i.e. the sum of the cross sections of the single branchings 44A and 44B) has a bigger or an equally big flow cross-section than the rest of the measurement device 100 so that no increased or only a slightly increased pressure resistance for the flow of the sample gas in the measurement device 100 is generated by the branchings 44. The lengths of the different branchings 44 through which the sample gas flows are chosen such that sample gas volumes of a certain volume size are optimally mixed. The mixing takes place exclusively passive and uses only the pressure difference to the outlet of the measurement device 100 which induces the sample gas to flow.

As an example, the application of the measurement device 100 for the breath analysis may be mentioned in which a single (in particular total) breath is homogenized. The exhalation generates the pressure difference which induces the sample gas to flow. The average volume of a breath is approximately 500 ml. Already at branchings 44 having three different diameter sizes with ratios d3:d2:d1=3:2:1 the laminar volume flow shows different velocities v3<v2<v1. If the total average of the single diameter sizes d1, d2 and d3 is held constant by choosing several branchings 44 having a diameter size d1 and d2, then approximately the same volume flows through all branchings 44 having the same diameter (disregarding friction). By means of the different flow velocities of the sample gas, the desired volume amount (e.g. 500 ml) can now be well mixed by choosing the branching length. The number of branchings 44 is at least 2. The more branchings 44 are used, the more homogeneous the sample gas can be mixed. A good mixing makes possible a more precise and faster measurement of gas components in the sample gas. It is important for e.g. highly precise measurements in flow-through measurement technique.

In an embodiment, the diameters of the single branchings 44 are chosen such that a second branching 44A has an at least 50%, in particular at least 60%, in particular at least 70%, in particular at least 80%, in particular at least 90% and very particular at least 100% bigger diameter than a first branching 44B.

Furthermore, the measurement chamber 2 has a connection 25 for the sample gas flowing out of the measurement chamber 2. Thereby, the sample gas flows e.g. through a tube 26 or the like to a spirometer 5, which determines the volumetric flow flowing through the measurement chamber 2. After flowing through the spirometer 5, the sample gas exits the measurement device into the surrounding, wherein the spirometer 5 can also be arranged at another location in the measurement device.

The sample device flows into the measurement chamber 2 perpendicular to the direction in which the laser light radiates the measurement chamber 2. Likewise, it flows out of the measurement chamber 2 also perpendicularly to the last mentioned direction. Thereby, the connections 24, 25 are arranged offset at the measurement housing.

The total measurement construction of the measurement device is an open construction without valves or air flaps which could hinder the flow of the sample gas. Rather, the sample gas can flow through the described construction unhindered. Thereby, provision is made that the cross section in the supply 43, the measurement chamber 2 as well as the drain 26 is essentially constant so that at all locations a laminar flow is guaranteed and no gas accumulations take place at certain locations. Rather, sample gas entering the measurement chamber 2 via the ante-chamber 4 completely replaces the sample gas previously present from the measurement construction. The sample gas flows through the ante-chamber 4 into the measurement chamber 2 and from the measurement chamber 2 through the spirometer 5 again out of the measurement device.

The measurements are carried out at normal pressure. The measurement chamber 2, the ante-chamber 4, the supply 43, the drain 26 and the spirometer 5 are designed such that they are tight up to an overpressure of up to 200 mbar compared to normal pressure. If no pressure difference between the gas inlet 24 and the gas outlet 25 is present, the sample gas can remain unmodified in the measurement chamber 2 up to several 10 minutes.

The infrared absorption measurements subsequently described in more detail are carried out in each phase of the gas flow through the measurement chamber 2, in particular also when the sample gas 2 flows through the measurement chamber 2. The measurements carried out are effected in real flow-through. Due to the open construction of the measurement chamber 2, the sample gas can be exchanged in the measurement chamber 2 as fast as desired.

As will be explained later on, the described measurement device is suited and can be arranged to measure the respiratory gas of a human or an animal as sample gas. In case of using respiratory gas as sample gas, the respiratory pressure arranges for that the new breath replaces the old breath from the measurement chamber and that thereby the new breath is measured in real time. Thus, the respiratory gas sample is exchanged in the measurement chamber only by the respiration for each patient individually as fast as necessary, wherein measurements are effected in real time in flow through. The respiratory resistance of the measurement apparatus is thereby designed such that it lies at less than 60 mbar for the gas flow.

The detectors 61, 62 are MCT-detectors. Such detectors are semi-conductor detectors on the basis of mercury(II) cadmium(II)tellurite. In an embodiment, the detectors 61, 62 are Peltier-cooled, whereby an abandonment of detectors cooled by liquid nitrogen is possible, at nonetheless high sensitivity. The abandonment of liquid nitrogen for cooling broadens the application area of the measurement device, e.g., in clinically daily routine.

Both detectors 61, 62 are virtually read out at the same time. Thereby, each detector 61, 62 measures the whole spectrum of the light emitted by the laser 1. Thereby, errors by variation of the detector sensitivity from detector to detector are avoided.

The signal read out by the detectors 61, 62 is first amplified and integrated in a repeater 7 for each detector 61, 62 separately. The amplified signal is then in each case, via an adapter 91, supplied to an evaluation unit 8 which is realized e.g. by a usual PC and suited software. Thereby, the signal of the detector 62 serves only for the standardization of the signal strength. Thus, intensity fluctuations at the detector 61 caused by intensity fluctuations of the laser 1 can be corrected by the signal of the detector 62. This increases the accuracy of the evaluation.

The evaluation unit 8 further receives signals from the spirometer 5. Provision can also be made that the temperature of the sample gas and/or the temperature in the measurement chamber 2 is communicated to the evaluation unit 8 via a non-depicted sensor or the temperature control 42, 27. A monitor 95 is assigned to the evaluation unit 8.

The evaluation unit 8 generates control signals to the laser control unit 92 in relation to the sweep signal, the laser temperature and the trigger frequency. The monitor 95 can serve for graphically depicting an evaluation of the conducted absorption measurements. The evaluation unit 8 can furthermore be connected to a telecommunications network, e.g. the internet and/or a telephone network.

A power supply 95 which is connected by a transformer 94 to a power plug arranges for electric supply of the different elements of the measurement device.

As explained, the frequency of the laser 1 is periodically varied. The spectral range thereby passed through is determined by the sweep voltage. At a laser rate of 50 kHz and a sweep voltage of 50 Hz, 1000 laser pulses can be measured per spectral range passed through. Thereby, the observed spectral range is measured 50 times per second. The measurements can also be averaged over a certain time, e.g. over the length of a breath.

The detector 61 is designed such that it carries out a single absorption measurement within $10^{-5}$ seconds or faster, in particular within $10^{-6}$ seconds or faster. A whole frequency range, i.e. the frequency range of the spectral range defined by the sweep voltage, can be scanned in approximately 0.002 to 1 second. In the mentioned exemplary embodiment, the point density per spectral range (per sweep) lies at 1000 points. Each laser pulse is detected and converted into a measuring point. Alternatively, the point density can be chosen lower, at approximately 500 points or also only 20 points per spectral range.

The high point density during passing through the measured spectral ranged connected with the small spectral line width of the laser 1 enables a spectral resolution of less than 0.02 cm$^{-1}$. This means that the absorption bands of the measured gas sample can be detected and analyzed very accurately. By deconvolution or other mathematic methods, the spectral resolution can be optionally further ameliorated.

Figure 2:
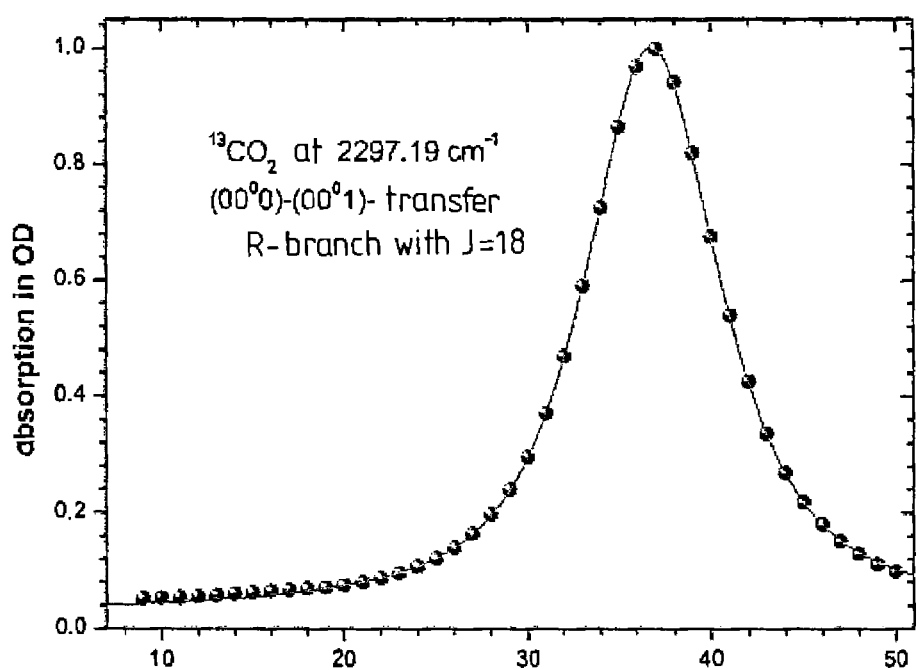
FIG. 2 shows the measurement of a $^{13}CO_2$ absorption line at 2297.19 $cm^{-1}$ by the measurement device of FIG. 1, wherein the absorption is illustrated in dependence on the frequency in wave numbers within a measured spectral range.

FIG. 2 shows the measurement of a $^{13}CO_2$ absorption line lying at a frequency (in wave numbers) of 2297.19 cm$^{-1}$. The abscissa indicates the variation of the frequency (due to the sweep voltage) with respect to the basic frequency of the laser 1. The absorption is indicated in OD (optical density). The point density is high enough to be able to determine the absorption line very accurate. Provision can be made to fit the curve. Fitting the absorption line can e.g. be effected with Lorenz curves.

The data acquisition is effected in each case by an analogue/digital card which is arranged in the evaluation unit 8 and acquires one data point or more per microsecond. Thereby, the resolution is better than 12 bit.

At a laser rate of 50 kHz, a modulation frequency of the sweep current of 50 Hz, 50 spectra per second are measured. 1000 points are measured per spectrum.

In an embodiment, the readout rate of the detectors 61, 62 is chosen such that it is twice as big as the laser rate. At a laser rate of 50 kHz, the readout rate of the detectors 61, 62 thus amounts to 100 kHz. This results in reading out a detected light signal only at every second triggering action. The measurements taking place in-between relate to the background or the noise, respectively. Reading out the detectors 61, 62 with the double laser rate makes it possible to immediately subtract the background at each light measurement. In an embodiment, this is effected in the evaluation unit 8 and further increases the accuracy of the measurement.

By the described measurement device absorption spectra are measured in real time for a defined spectral range since a plurality of spectra can be recorded per second. Optionally, a plurality of spectra can be averaged, thus further increasing the accuracy of the measurement. Therewith, a real-time detection of modifications of the composition of the sample gas is made possible.

To obtain a high accuracy, a high frequency stability is necessary. This is achieved by readjusting the temperature control of the laser control unit 92 by a measurement software. Thereby, the temperature is corrected in small steps so that always the same gas absorption maximum (e.g. of $^{12}CO_2$) is located at the same position in the measurement range. Furthermore, provision is made that also the sweep voltage is corrected so that the further absorption lines are located at the desired position in the measurement range. Thereby, the measurements become optimally reproducible and can be averaged. The signal to noise ratio is ameliorated by large averaging numbers. In an embodiment, the measurement software also permits an automatic detection if the laser power decreases and when the laser 1 fails. The according measurement software can be part of the evaluation unit 8 or of the laser control unit 92.

Furthermore, provision can be made that a fast evaluation of the spectra by an integration of special frequency ranges is effected which are to assign to single absorption lines. Recording straight calibration lines with gas samples, the composition of which is known, thereby permits the simple and accurate determination of the offset without fitting the data. Since the frequency stability is reproducibly adjusted, frequency ranges can be selectively addressed from which the concentrations can be determined highly precise. Fitting the high amount of data would potentially slow down the measurement process and is therefore not compulsory necessary.

Due to the high selectivity of the measurement, the measurement can be effected independent on sample gases like oxygen or other narcotic gases. Influences of any other gas can be separated with the present high spectral resolution.

In the illustrated exemplary embodiment, the measurement device is optimized to carry out liver capacity measurements after application of $^{13}C$-labelled methacetin. The additionally metabolized $^{13}CO_2$ is detected in the breath.

This is described in detail in WO 2007/000145 A2 to which reference is made in this respect.

Figure 7:
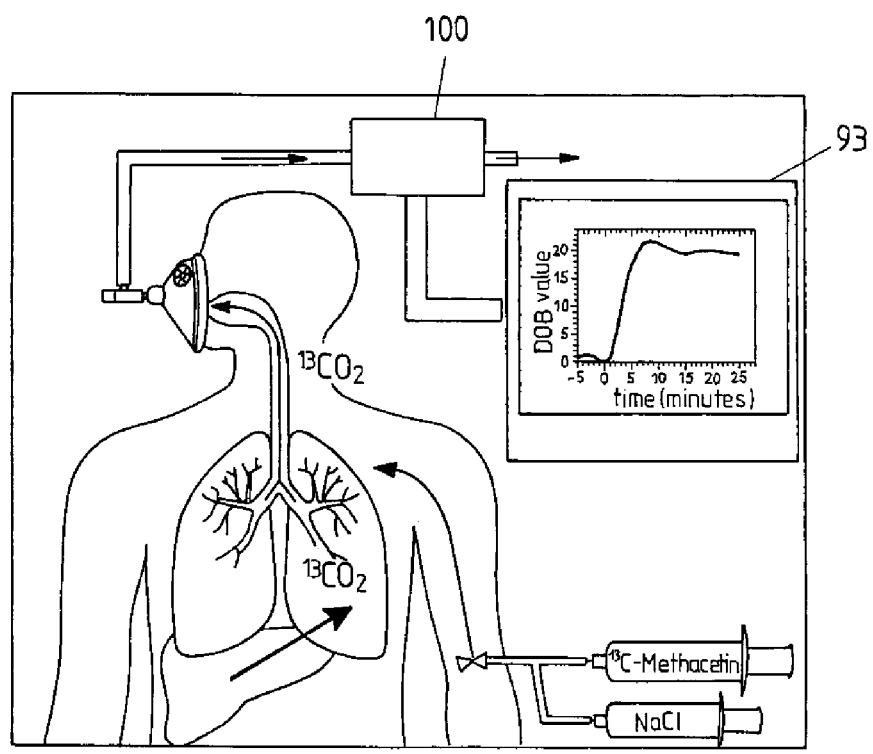
FIG. 7 shows a schematic depiction of a measurement course for determining the liver performance by using the measurement device of FIG. 1.

As is schematically illustrated in FIG. 7, a patient to be examined carries a respiratory mask comprising an air inlet valve and an air outlet valve. Thereby, the inhalation air is separated from the exhalation air. Exhaled air cannot be again inhaled. A plastic tube is connected to the air outlet valve, the plastic tube guiding the whole breath to the measurement device 100 and being connected to the ante-chamber 4. The mask and the tubing are also tight up to an overpressure of up to 200 mbar so that the whole respiratory air flows through the measurement device 100.

Thereby, a measurement software automatically detects if the mask does not correctly sit on the patient's face or got out of place. The measurement software also detects whether or not the patient breathes and optionally issues a warning. Furthermore, provision is made that the measurement software detects when the measurement can be terminated. Such a measurement software can also be integrated into the evaluation unit 8.

The laser frequency of the laser 1 and the spectral range defined by the sweep voltage are now chosen such that at least two absorption lines of the sample gas are positioned within the defined spectral range. In the considered example, these are one absorption line of $^{13}CO_2$ and one absorption line of $^{12}CO_2$. After application of $^{13}C$-labelled methacetin, this is degraded in the liver and can be detected in the respiratory air. The degradation correlates with an increase of $^{13}CO_2$ in the respiratory air which leads to a modified ratio of $^{13}CO_2$ to $^{12}CO_2$. The ratio is determined by the measurement device 100 on the basis of absorption measurements and its time evolution is illustrated on a monitor 93.

Figure 3:
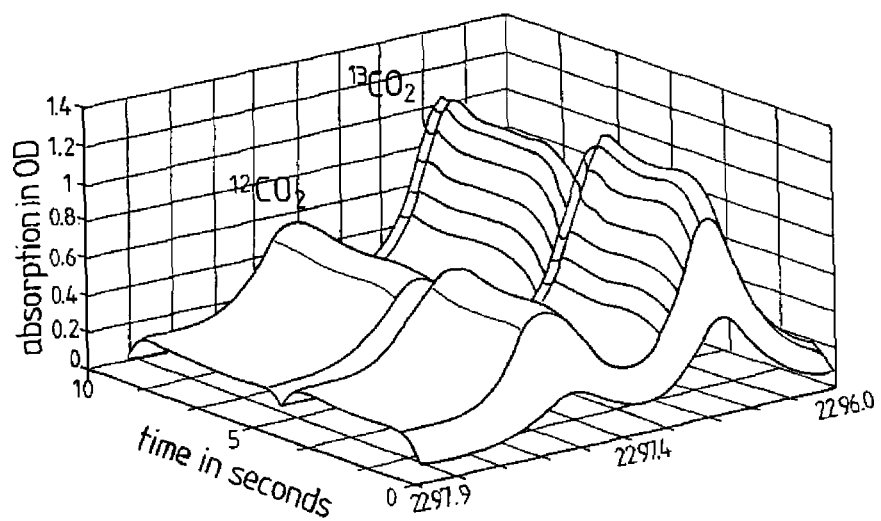
FIG. 3 shows the concomitant measurement of the $^{12}CO_2$ and the $^{13}CO_2$ absorption lines in the course of two consecutive breaths, wherein the absorption is on the one hand illustrated over time and on the other hand over the frequency in wave numbers.

FIG. 3 shows the concomitant measurement of the $^{12}CO_2$ and $^{13}CO_2$ absorption lines in the evolution of two consecutive breaths. The absorption variation is displayed in OD (optical density). It is recorded and depicted both against the time in seconds and also against the frequency in wave numbers. Strong variations of the absorption and therewith of the concentration are clearly visible.

Figure 4:
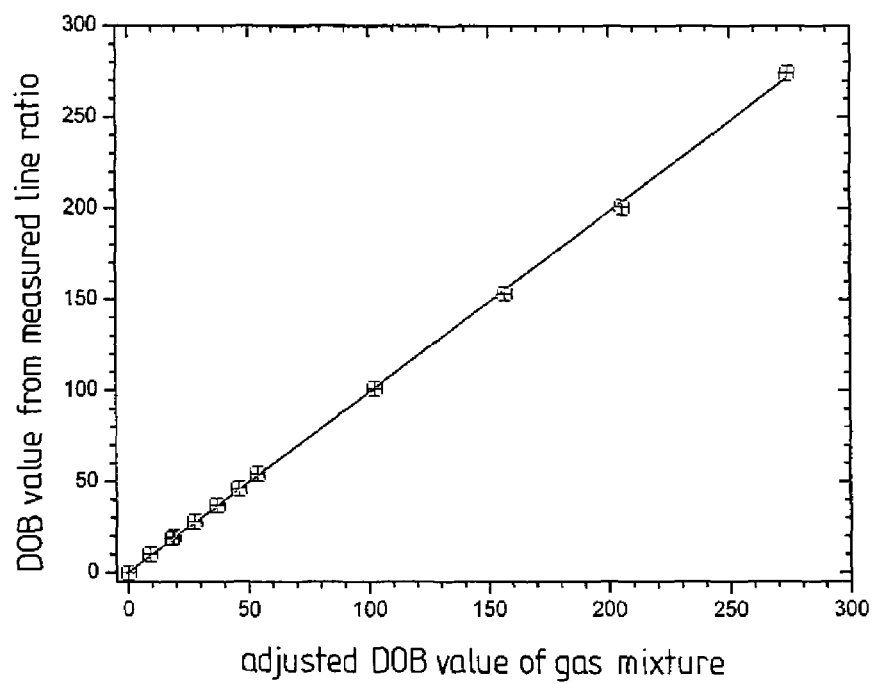
FIG. 4 shows the ratio of $^{13}CO_2$ to $^{12}CO_2$ concentration in the measurement range between 0 DOB and 300 DOB, wherein the abscissa represents an adjusted concentration ratio of sample gases and the ordinate represents values measured by the measurement device of FIG. 1.

FIG. 4 clarifies the accuracy by which the ratio of the $^{13}CO_2/^{12}CO_2$ concentration can be measured. The concentration ratios were adjusted with very precisely characterized sample gases and these ratios were verified by test measurements. Thereby, the abscissa shows a DOB value adjusted by test gases. The ordinate shows a measured DOB value being determined from the line ratios according to FIG. 3. Thereby, 1 DOB denotes a variation of the $^{13}CO_2$ to $^{12}CO_2$ ratio by one thousandth over the natural ratio. It was shown that the ratio of the $^{13}CO_2$ to $^{12}CO_2$ concentration can be determined with an accuracy of better than 5 DOB per breath—at a measurement of several consecutive breaths.

The measurement range extends from 0 DOB to over 1000 DOB in a concentration range of 0.08% to 8% $CO_2$. Over the whole range, the ratio is measured with highest accuracy.

Figure 5:
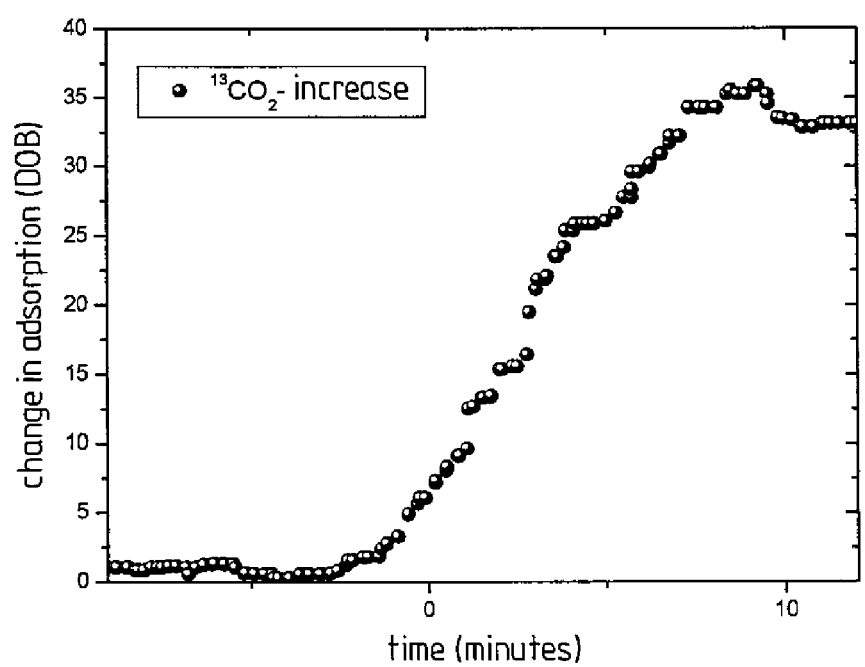
FIG. 5 shows the $^{13}CO_2$ increase of a test person after intake of $^{13}C$-labelled methacetin in dependence on time.

FIG. 5 shows the liver capacity determination after intake of $^{13}C$-labelled methacetin. The $^{13}CO_2$ increase of a test person after intake, which is accompanied by an increased absorption variation of the $^{13}CO_2$ absorption line, is depicted. Each breath was measured and corresponds to a measuring point (i.e. the spectra measured during a breath and the ratio determined from those spectra were averaged to a measuring point). The increase and the maximum of the absorption variation can be clearly and quantitative exactly determined. The diagnostic was applied approximately at −3 minutes.

In an according way, also the ratio of other isotopes, elements or molecules can be determined.

The measurement device according to an aspect of the invention permits, besides the measurement of the ratio distinct isotopes, also other evaluations. E.g., the total amount of a metabolism product, e.g. of $^{13}CO_2$ in breath, can be measured. Thus, the volumetric flow flowing through the measurement chamber 2 is determined with the spirometer 5. Since the volume of the measurement chamber 2 is constant and the absorption is determined in a time-resolved manner, the carbon dioxide amount flowing through the measurement chamber can be determined by integration over time. In particular, the concentration can be determined directly from the absorption since the extinction coefficient is known for each absorption line, just as the length of the measurement chamber. Since the measurement device permits to detect the absorption in a time-resolved manner in real time and also the volumetric flows in a time-resolved manner in real time, the total amount can be determined by an integration of the product of volume and concentration over time in real time.

Due to the measurement of the $^{13}CO_2$ concentration and the $^{12}CO_2$ concentration, the carbon dioxide amount being present in the measurement chamber can thus be determined separately for $^{13}CO_2$ and $^{12}CO_2$. In particular, the total amount of $^{13}CO_2$ can be determined up to 10 μg accurate per breath—upon measurement of several consecutive breaths.

A further application determines the detection of the variation of the $CO_2$ absorption lines at varying concentration of the $CO_2$ in the respiratory air, at constant pressure in the respiratory air.

With increasing gas concentration and/or varying partial pressure, the line width of the absorption lines is modified by line broadening mechanisms known per se. The line width can also be measured at distinct known $CO_2$ concentrations by the measurement device, cf. the absorption lines of FIGS. 2 and 3.

Figure 6:
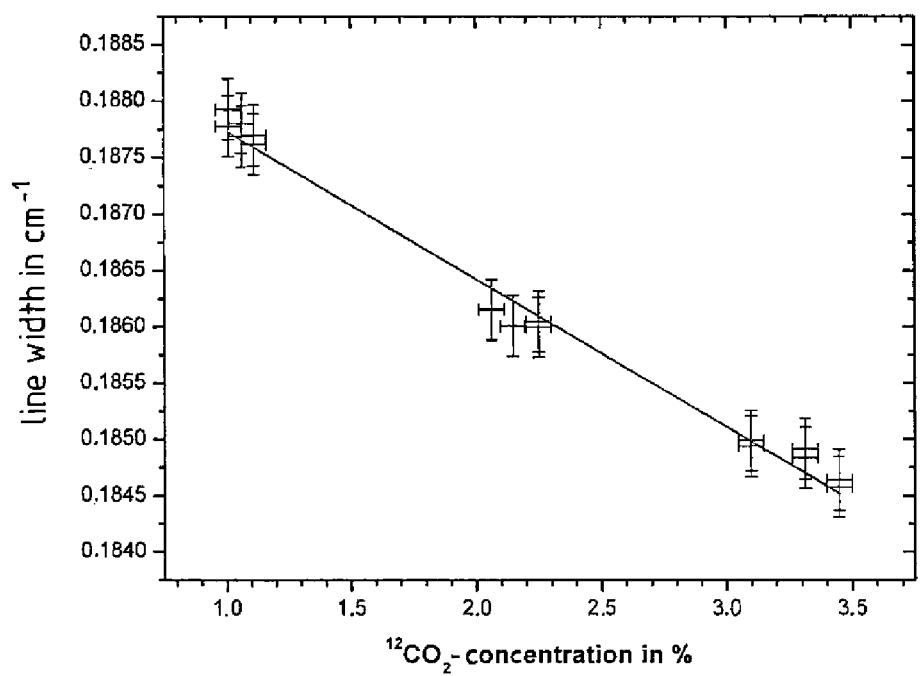
FIG. 6 shows the line widths of $CO_2$ absorption lines in dependence on the $CO_2$ concentration of the sample gas at a constant pressure.

FIG. 6 shows the measured line widths in dependence on the $^{12}CO_2$ concentration of the respiratory gas in percent. The determined dependency can be evaluated for further error reduction.

The frequency range for the measurement of $^{13}CO_2$ and $^{12}CO_2$ lies between 2200 and 2400, in particular at 2295 to 2305 cm$^{-1}$. Generally, a laser 1 is used in an embodiment which emits light in the frequency range between 2 μm to 12 μm.

The use of the described measurement device is not limited to the measurement of the $CO_2$ content in the respiratory air. Any gas sample can be analyzed by the described measurement apparatus. Thereby, e.g. an isotopic ratio of any gases can be determined highly sensitive and very accurate in real time. The measurement device according to an aspect of the invention enables a quantitative, dynamic and time-resolved measurement of metabolic parameters in real time. Thereby, also stress analyses of a human or animal can be carried out in real time.

The invention claimed is:

1. A measurement device for analyzing a sample gas by infrared absorption spectroscopy, comprising:
   an ante-chamber configured to homogenize the sample gas to be analyzed,
   a measurement chamber arranged to receive homogenized sample gas from the ante-chamber,
   a laser being arranged in relation to the measurement chamber such that light being emitted from the laser radiates through the measurement chamber, wherein the light being emitted from the laser has a frequency in a range of from $2.498*10^7$ MHz to $1.499*10^8$ MHz, a detection device detecting the light being emitted from the laser and radiated through the measurement chamber, and an evaluation unit evaluating signals generated by the detection device regarding a light absorption occurred in the measurement chamber, wherein the ante-chamber has a single inlet through which the sample gas enters the ante-chamber and at least two branchings of different length and diameter through which parts of the sample gas pass through, wherein the sample gas from the single inlet is separated into the parts of the sample gas by the at least two branchings and the parts of the sample gas are brought together again after the at least two branchings, a total cross section of the at least two branchings being equal to or greater than a cross-section of a single tube that delivers the homogenized sample gas from the ante-chamber to the measurement chamber, wherein the laser is a narrowband emitting laser having a line width of less than $0.2$ cm$^{-1}$ and being smaller than or equal to a width of an infrared absorption line to be measured of the homogenized sample gas, wherein the laser is designed and arranged such that the laser frequency is varied periodically within a defined spectral range having a width of between $0.5$ cm$^{-1}$ and $60$ cm$^{-1}$, wherein the laser frequency and its variation are chosen such that at least two infrared absorption lines to be measured of the homogenized sample gas lie in the defined spectral range, wherein the evaluation unit is designed and arranged to determine a ratio of two isotopes of the homogenized sample gas on the basis of the light absorptions occurring at two absorption lines, wherein the detection device is designed and arranged such that it detects the light being emitted from the laser and radiated through the measurement chamber in such a time-resolved manner that the light absorption can be determined frequency-resolved within the defined spectral range, wherein the detection device carries out a single absorption measurement within $10^{-5}$ s or faster, wherein the measurement device is suited and can be arranged to measure the respiratory gas of a human or animal as sample gas, wherein the measurement chamber has an open construction devoid of obstructions which could hinder the flow of the homogenized sample gas, wherein the measurement device has a constant cross section for the sample gas flowing through so that a laminar flow of sample gas is established in the measurement device, wherein the respiratory gas exchanges in the measurement chamber only by the respiration of the human or animal, and wherein the respiratory resistance of the measurement device is less than 60 mbar.

2. The measurement device according to claim 1 wherein the evaluation unit is designed and arranged to determine the ratio of two isotopes in real time.

3. The measurement device according to claim 1, wherein the measurement chamber is mirror-less and light emitted from the laser passes through the measurement chamber exactly once.

4. The measurement device according to claim 3, wherein the measurement chamber has an inlet window through which the laser light enters the measurement chamber and an outlet window through which the transmitted light exits the measurement chamber.

5. The measurement device according to claim 1, wherein furthermore tempering means for tempering the measurement chamber onto a constant temperature are provided.

6. The measurement device according to claim 1, wherein the homogenized sample gas flows through the measurement chamber continuously or intermittently and wherein the measurement chamber has an open construction without valves or air flaps which would hinder the flow of the homogenized sample gas into and out of the measurement chamber.

7. The measurement device according to claim 6, wherein the measurement device is designed and arranged such that a time-resolved light detection by the detection device occurs during flowing-through of the homogenized sample gas through the measurement chamber.

8. The measurement device according to claim 1, having a spirometer detecting the volumetric flow rate of the homogenized sample gas flowing through the measurement chamber.

9. The measurement device according to claim 1, wherein the laser signal is pulsed with a pulse duration of less than 200 ns.

10. The measurement device according to claim 9, wherein the detection device is designed and arranged to be read out with a frequency that is twice as big as the frequency by which the laser emits light pulses.

11. The measurement device according to claim 1, wherein the measurement device is formed such that the light emitted from the laser is divided into two partial beams, wherein a first of the two partial beams passes through the measurement chamber and a second of the two partial beams is detected by a reference detection device, and wherein the evaluation unit evaluates the signals of the reference detection device for standardizing the signal intensity of the laser.

12. The measurement device according to claim 1, wherein the measurement device is designed and arranged to determine the ratio of the $^{13}CO_2/^{12}CO_2$ isotope concentration in the respiratory gas of a human or animal in a time-resolved manner.

13. The measurement device according to claim 1, wherein the measurement device is designed and arranged to conduct a quantitative measurement of a metabolic parameter in the respiratory gas in real time.

14. The measurement device according to claim 1, wherein the measurement device is designed and arranged to determine the carbon dioxide concentration of the respiratory gas in the range between 0.08% and 8% in flow-through in real time.

15. A method for analyzing a sample gas by infrared absorption spectroscopy in a measurement device according to any of the preceding claims, having the steps of:

homogenizing a sample gas in an ante-chamber having a single inlet through which the sample gas enters the ante-chamber and at least two branchings of different length and diameter through which parts of the sample gas pass through, wherein the sample gas from the single inlet is separated into the parts of the sample gas by the at least two branchings and the parts of the sample gas are brought together again after the at least two branchings, a total cross section of the at least two branchings being equal to or greater than a cross-section of a single tube that delivers the homogenized sample gas from the ante-chamber to a measurement chamber, radiating the measurement chamber with light being emitted from a narrowband laser having a line width of less than 0.2 cm$^{-1}$, and being smaller than or the width of an infrared absorption line to be measured of the homogenized sample gas being present in the measurement chamber, wherein the measurement chamber has an open construction devoid of obstructions which could hinder the flow of the homogenized sample gas, wherein the light being emitted from the laser has a frequency lying in a rage of from 2.498*10$^7$ MHz to 1.499*10$^8$ MHz, wherein the laser frequency is varied periodically within a defined spectral range of between 0.5 cm$^{-1}$ and 60 cm$^{-1}$, and the laser frequency and its variation are chosen such that at least two infrared absorption lines to be measured of the homogenized sample gas lie in the defined spectral range, time-resolved detecting the light emitted from the laser and radiated through the measurement chamber, wherein a single absorption measurement is carried out within 10$^{-5}$ s or faster, and evaluating the detected signals regarding a light absorption occurred in the measurement chamber, wherein the light absorption is determined frequency-resolved within the defined spectral range, wherein a ratio of two isotopes of the homogenized sample gas on the basis of the light absorptions occurring at two absorption lines is determined, wherein the homogenized sample gas is the respiratory gas of a human or animal, wherein the respiratory gas is exchanged in the measurement chamber only by the respiration of the human or animal, wherein the respiratory resistance of the measurement device is less than 60 mbar, and wherein the measurement device has a constant cross section for the sample gas flowing through so that a laminar flow of sample gas is established in the measurement device.

16. The method according to claim 15, wherein the ratio of two isotopes of the homogenized sample gas is determined which have absorption lines lying within the defined spectral range.

* * * * *